United States Patent
Parramon et al.

(10) Patent No.: US 8,081,925 B2
(45) Date of Patent: Dec. 20, 2011

(54) TRANSCEIVER FOR AN IMPLANTABLE MEDICAL DEVICE HAVING SWITCHABLE SERIES-TO-PARALLEL TANK CIRCUIT

(75) Inventors: Jordi Parramon, Valencia, CA (US); Kiran Nimmagadda, Valencia, CA (US); Md Mizanur Rahman, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 895 days.

(21) Appl. No.: 12/117,487

(22) Filed: May 8, 2008

(65) Prior Publication Data

US 2009/0281597 A1    Nov. 12, 2009

(51) Int. Cl.
*H04B 5/00* (2006.01)
*H04M 1/00* (2006.01)

(52) U.S. Cl. .................................. 455/41.1; 455/575.6

(58) Field of Classification Search .................. 455/569, 455/572, 575.1, 575.2, 575.6, 73, 90.1–90.3, 455/95, 41.1–41.3, 569.1, 169.1, 195.1, 262; 307/15

See application file for complete search history.

(56) References Cited

U.S. PATENT DOCUMENTS

| | | | |
|---|---|---|---|
| 4,847,617 A | 7/1989 | Silvian |
| 5,264,843 A | 11/1993 | Silvian |
| 5,999,857 A | 12/1999 | Weijand et al. |
| 6,023,641 A | 2/2000 | Thompson |
| 6,091,987 A | 7/2000 | Thompson |
| 6,115,636 A | 9/2000 | Ryan |
| 6,163,721 A | 12/2000 | Thompson |
| 6,167,303 A | 12/2000 | Thompson |
| 6,185,454 B1 | 2/2001 | Thompson |
| 6,185,460 B1 | 2/2001 | Thompson |
| 6,223,080 B1 | 4/2001 | Thompson |
| 6,236,888 B1 | 5/2001 | Thompson |
| 6,324,426 B1 | 11/2001 | Thompson |
| 6,434,425 B1 | 8/2002 | Thompson |
| 6,438,422 B1 | 8/2002 | Schu et al. |
| 6,496,729 B2 | 12/2002 | Thompson |
| 6,516,227 B1 | 2/2003 | Meadows et al. |
| 6,535,766 B1 | 3/2003 | Thompson et al. |
| 6,539,253 B2 | 3/2003 | Thompson et al. |
| 6,567,703 B1 | 5/2003 | Thompson et al. |
| 6,868,288 B2 | 3/2005 | Thompson |
| 6,889,084 B2 | 5/2005 | Thompson et al. |

(Continued)

FOREIGN PATENT DOCUMENTS

WO    91/16696    10/1991
WO    00/24456    5/2000

OTHER PUBLICATIONS

International Search Report for corresponding application No. PCT/US2009/039574, dated Nov. 16, 2009.

*Primary Examiner* — Eugene Yun (74) *Attorney, Agent, or Firm* — Wong, Cabello, Lutsch, Rutherford & Brucculeri, LLP (57) ABSTRACT

An improved transceiver circuit particularly useful in an inductively coupled wireless communication system such as an implantable medical device system is disclosed. The improved transceiver circuit is switchable to assume a serial L-C configuration in the transmit mode and a parallel L-C configuration in the receive mode, but does not require high voltage switches. A low-drive transmitter and a high-input-impedance receiver are used, which reduces power consumption in receive mode, while still maintaining good transmitter performance.

27 Claims, 7 Drawing Sheets

U.S. PATENT DOCUMENTS

| | | |
|---|---|---|
| 7,177,698 B2 | 2/2007 | Klosterman et al. |
| 2002/0026224 A1 | 2/2002 | Thompson et al. |
| 2002/0035383 A1 | 3/2002 | Thompson |
| 2002/0045920 A1 | 4/2002 | Thompson |
| 2002/0173825 A1 | 11/2002 | Thompson |
| 2003/0014082 A1 | 1/2003 | Schu et al. |
| 2004/0015199 A1 | 1/2004 | Thompson et al. |
| 2004/0039423 A1 | 2/2004 | Dolgin |
| 2005/0111682 A1 | 5/2005 | Essabar et al. |

TRANSCEIVER FOR AN IMPLANTABLE MEDICAL DEVICE HAVING SWITCHABLE SERIES-TO-PARALLEL TANK CIRCUIT

FIELD OF THE INVENTION

The present invention relates to transceiver circuitry useable in an implantable medical device system.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. Pat. No. 6,516,227, which is incorporated herein by reference in its entirety.

Figures 1A, 1B:
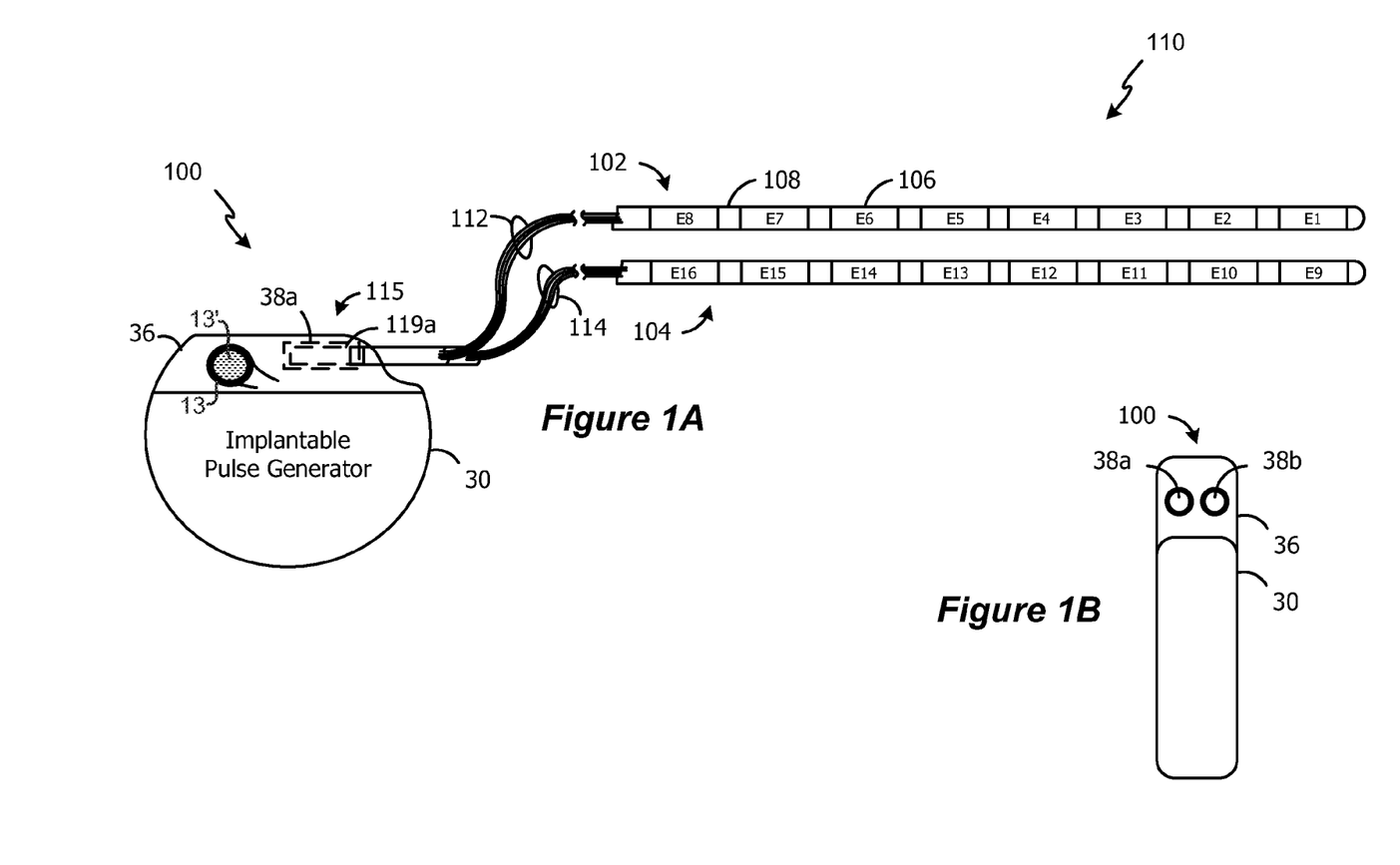
FIGS. 1A and 1B show an implantable pulse generator (IPG), and the manner in which an electrode array is coupled to the IPG in accordance with the prior art.

Spinal cord stimulation is a well-accepted clinical method for reducing pain in certain populations of patients. As shown in FIGS. 1A and 1B, a SCS system typically includes an Implantable Pulse Generator (IPG) 100, which includes a biocompatible case 30 formed of titanium for example. The case 30 typically holds the circuitry and power source or battery necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary.

Figure 2:
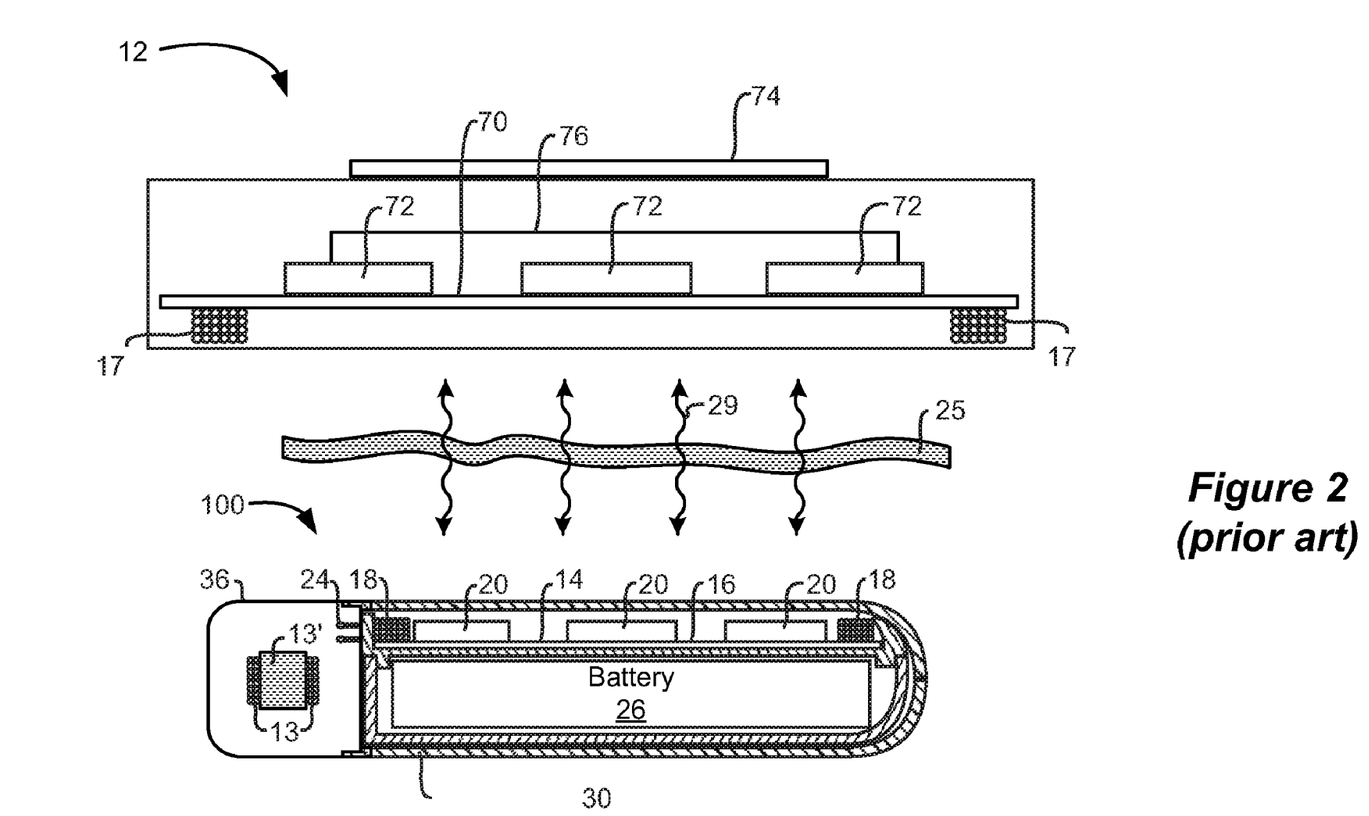
FIG. 2 shows the relation between the IPG of FIG. 1 and an external controller with which it communicates via electromagnetic inductive coupling.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from an external controller 12 as explained further below; and a charging coil 18 for charging or recharging the IPG's power source or battery 26 using an external charger (not shown). The telemetry coil 13 can be mounted within the header connector 36 as shown.

As just noted, an external controller 12, such as a hand-held programmer or a clinician's programmer, is used to send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12.

Wireless data transfer between the IPG 100 and the external controller 12 takes place via inductive coupling. To implement such functionality, both the IPG 100 and the external controller 12 have coils 13 and 17 respectively. Either coil can act as the transmitter or the receiver, thus allowing for two-way communication between the two devices. When data is to be sent from the external controller 12 to the IPG 100 for example, coil 17 is energized with alternating current (AC), which generates a magnetic field 29, which in turn induces a voltage in the IPG's telemetry coil 13. The power used to energize the coil 17 can come from a battery 76, which like the IPG's battery 26 is preferably rechargeable, but power may also come from plugging the external controller 12 into a wall outlet plug (not shown), etc. The induced voltage in coil 13 can then be transformed at the IPG 100 back into the telemetered data signals. To improve the magnetic flux density, and hence the efficiency of the data transfer, the IPG's telemetry coil 13 may be wrapped around a ferrite core 13'.

As is well known, inductive transmission of data from coil 17 to coil 13 can occur transcutaneously, i.e., through the patient's tissue 25, making it particular useful in a medical implantable device system. During the transmission of data, the coils 13 and 17 lie in planes that are preferably parallel. Such an orientation between the coils 13 and 17 will generally improve the coupling between them, but deviation from ideal orientations can still result in suitably reliable data transfer.

To communicate a serial stream of digital data bits via inductive coupling, some form of modulation is generally employed. In a preferred embodiment, Frequency Shift Keying (FSK) can be employed, in which the logic state of a bit (either a logic '0' or a logic '1') corresponds to the frequency of the induced magnetic field 29 at a given point in time. Typically, this field has a center frequency (e.g., fc=125 kHz), and logic '0' and '1' signals comprise offsets from that center frequency (e.g., f0=121 kHz and f1=129 kHz respectively). Once the data is modulated in this manner at the transmitting device (e.g., the external controller 12), it is then demodulated at the receiving device (e.g., the IPG 100) to recover the original data. While FSK modulation may be preferred for a given application, one skilled in the art will recognize that other forms of data modulation (e.g., amplitude modulation, On-Off-Keying (OOK), etc.) can be used as well. These modulation schemes as used in a medical implantable device system are disclosed in U.S. Pat. No. 7,177,698, which is incorporated herein by reference in its entirety, and because they are well known, they are not further discussed.

Figures 3A, 3B:
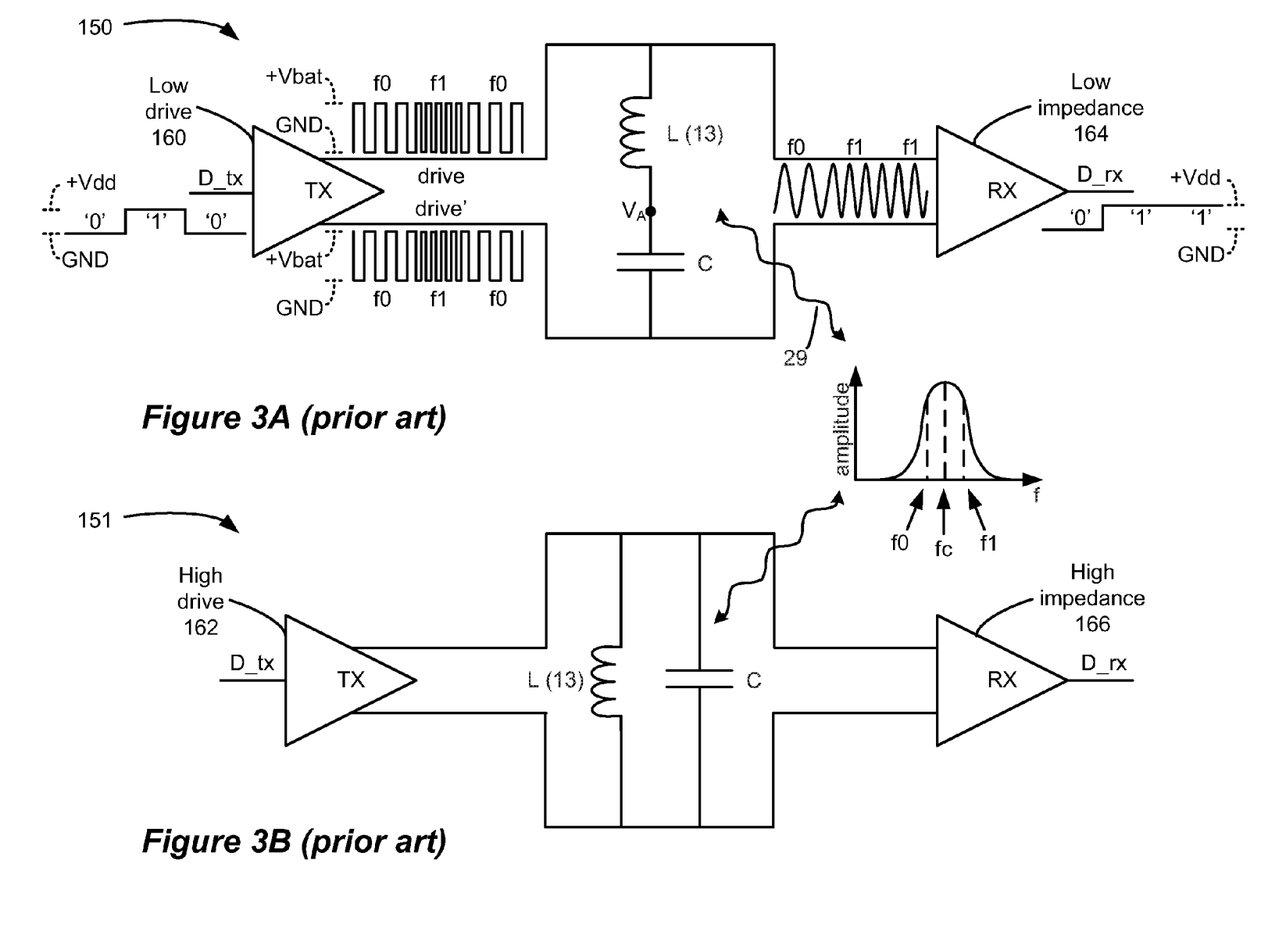
FIGS. 3A and 3B show prior art transceiver circuits useable in IPGs to communicate with an external controller.

Typical transceiver circuits 150 and 151 for effecting the transmission and reception of data in the manners just described are shown in FIGS. 3A and 3B. In the example shown, it is assumed that the transceiver circuits 150 and 151 are within the IPG 100, although it should be remembered that such circuitry may also be present in the external controller 12. Each circuit comprises a transmitter (TX), an L-C resonant circuit (or as it is sometimes known in the art, a "tank circuit"), and a receiver (RX). In both cases, the inductor (L) in the tank circuit comprises the IPG's data communication coil 13 discussed previously. In circuit 150 (FIG. 3A), the inductor L and capacitor C are connected in series; in circuit 151 (FIG. 3B), the inductor L and capacitor C are in parallel.

In either case, transmission and reception is effected in essentially the same way. As shown in the example of FIG. 3A, the transmitter TX modulates a digital input, D_tx, to produce two complementary drive signals (drive and drive'), which are applied across the resonant circuit. The digital input is referenced to the basic digital power supply operating in the IPG, Vdd, which may be about 2.8V. The magnitude of the drive signals, by contrast, are referenced to Vbat, i.e., the voltage of the battery 26 in the IPG 100, which may be about 3.0 to 4.2V. (Usually the power supply voltage, Vdd, is derived by a regulator from the battery voltage, Vbat, but this is not strictly necessary, and these voltages can be one and the same, and either can power either the transmitter or the receiver. For the purpose of this disclosure, either Vdd or Vbat may be considered as a power supply voltage). Because the drive signals are complimentary, +Vbat and ground are alternatively applied across the resonant circuit, causing the desired resonance to produce the magnetic field 29. When receiving, the receiver RX receives differential inputs caused by the resonance of the resonance circuit, which is then demodulated to form the digital output D_rx, which is again referenced to Vdd (or Vbat, again, either of these voltages can be considered the power supply voltage that powers the receiver). The circuitry for transmitters TX and receivers RX are well known, and hence are not further discussed.

Each of these series and parallel tank circuits has advantages and disadvantages. For example, the series-connected L-C tank 150 is capable of forming large voltages across the inductor, L during transmission. In other words, the voltage produced at the node between the inductor and the capacitor, $V_A$, is amplified by the Q (quality factor) of the tank which can equal about +/−50V or so. This improves the magnitude of the magnetic field 29 which is produced, and thus ultimately improves the transmitter performance. As a result, a low voltage drive transmitter 160 can be used that drives the resonant circuit with smaller voltage signals compatible with standard CMOS integrated circuit technology. By contrast, the receiver RX in the series configuration is generally desired to have a relatively low input impedance 164 (e.g., <10 ohms) to enhance detection of the voltage induced in the resonant circuit by the received magnetic field 29. Unfortunately, the simultaneous desires for a high transmit field and low receiver input impedance increases the power consumption in the receiver RX. Increased receiver power consumption in the IPG 100 is especially problematic due when one considers that IPG batteries 26 (FIG. 2) are relatively small and therefore of limited capacity.

By contrast, the transmit field in the parallel-connected transceiver circuit 151 is not as high, because the voltages across the inductor are limited to the magnitude of the drive signals. As a result, a high drive transmitter 162 is required, which requires drive signals of greater magnitude (+/−50V or so), and which is not compatible with standard CMOS integrated circuit technology. However, the benefit to the parallel configuration occurs on the receiver side. Specifically, the receiver can have a relatively high input impedance 166 (e.g., >10 k ohms) compared to the low impedance receiver 164 used in the series configuration, resulting in lower power consumption and increased detection sensitivity in the receiver.

DETAILED DESCRIPTION

The description that follows relates to use of the invention within a spinal cord stimulation (SCS) system. However, it is to be understood that the invention is not so limited. Rather, the invention may be used with any type of implantable medical device system that could benefit from more-efficient communications between an external controller and the device. For example, the present invention may be used as part of a system employing an implantable sensor, an implantable pump, a pacemaker, a defibrillator, a cochlear stimulator, a retinal stimulator, a stimulator configured to produce coordinated limb movement, a cortical and deep brain stimulator, or in any other neural stimulator configured to treat any of a variety of conditions.

The inventors realize from the prior art transceiver circuits 150 and 151 of FIGS. 3A and 3B that an optimal transceiver circuit would have a serial L-C configuration while transmitting and a parallel L-C configuration while receiving. However, the inventors also realize that such a solution requires more than merely designing a switching network to affect such a series-to-parallel conversion. This is because high voltages (e.g., upward of 100V peak-to-peak) can be formed in the resonant tank circuit. For example, and as previously mentioned, the voltage at the node between the inductor and capacitor, $V_A$, can be +/−50 V or so. Accordingly, a mere switching network would require such switches to handle high voltages without breaking or punching through. Such high voltage switches are not easily formed using the types of integrated circuits typically used in the IPG 100, particularly when one considers that space is generally limited in the IPG.

Figure 4:
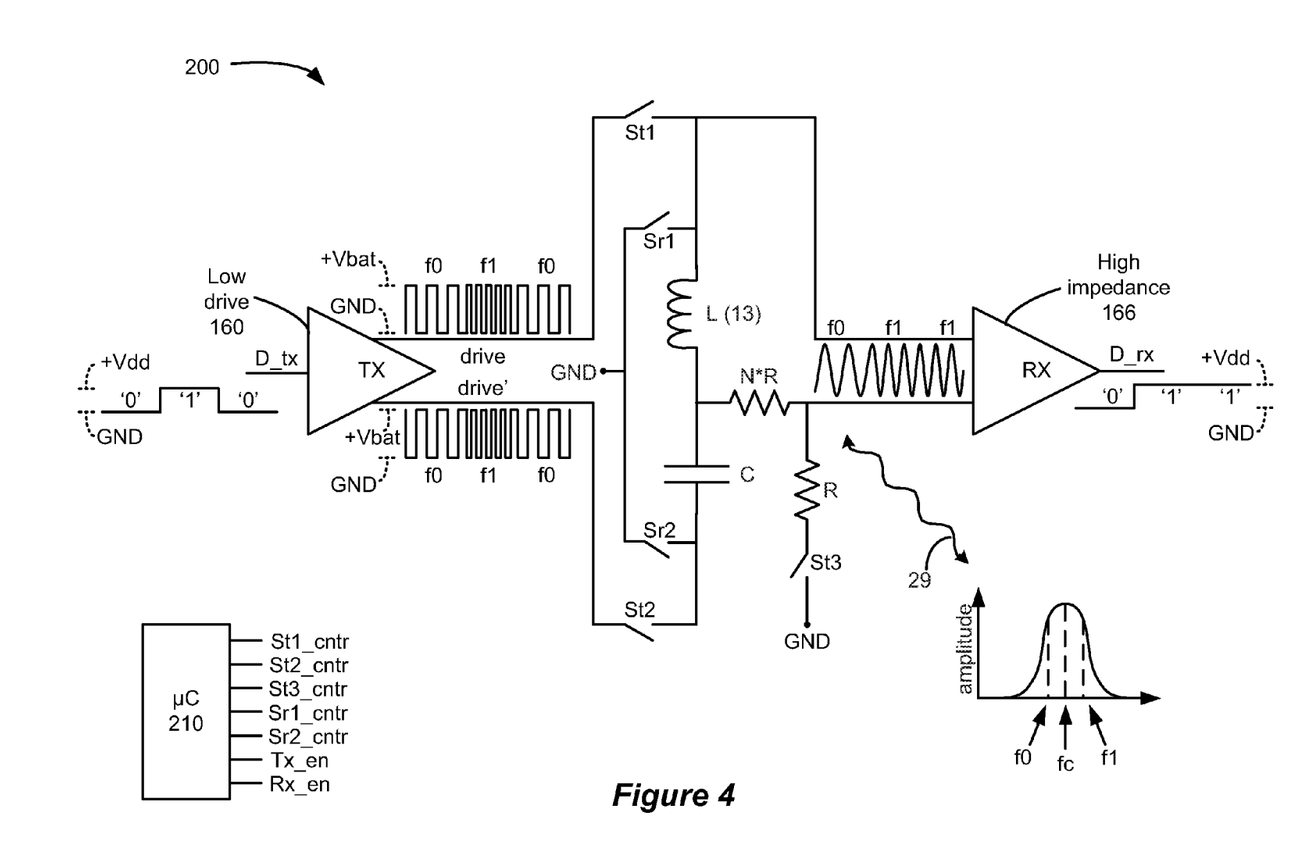
FIG. 4 shows an embodiment of the disclosed improved transceiver circuit.

The disclosed solution therefore comprises an improved transceiver circuit 200 that is switchable to assume a serial L-C configuration in the transmit mode and a parallel L-C configuration in the receive mode, but does not require high voltage switches. An embodiment of the improved transceiver circuit 200 is shown in FIG. 4. Note that the improved transceiver circuit 200 borrows the low drive transmitter 160 from the series-configuration prior art transceiver 150 (FIG. 3A) and the high impedance receiver 166 from the parallel-configuration prior art transceiver 151 (FIG. 3B). Again, the structure of such a low drive transmitter 160 and high impedance receiver 166 are well known to those of skill in the art and need not be set forth here. The values for the inductor L and capacitor C can vary depending on designer preference, but in one embodiment can comprise 290 microHenries and 5.6 nanoFarads respectively.

Shown further in FIG. 4 is the microcontroller 210 used to control the improved transceiver circuit 200. While the microcontroller 210 would control many different functions in the IPG 100, only those control signals relevant to the transceiver 200 are illustrated. Specifically illustrated are two enable control signals for the transceiver 160 (Tx_en) and receiver 166 (Rx_en), and five control signals for closing various switches associated with the L-C resonant circuit. Three of the switches, St1, St2, and St3 are controlled by their respective control signals, St1_cntr, St2_cntr, and St3_cntr, to be closed while the transceiver 200 is transmitting, while two of the switches, Sr1 and Sr2, are controlled by their respective control signals, Sr1_cntr and Sr2_cntr, to be closed while the transceiver 200 is receiving. Although shown as separate control signals for simplicity, it should be understood the transmitter enable signal, Tx_en, and related transmitter switch control signals, St1_cntr, St2_cntr, and St3_cntr, could comprise a single signal, while the receiver enable signal Rx_en and related receiver switch control signals, Sr1_cntr and Sr2_cntr, could comprise a single signal.

Because the improved transceiver circuit 200 uses both a low drive transmitter 160 and a high impedance receiver 166, it is respectful of receiver power consumption, and hence well suited for implementation in an IPG 100, in which power capacity is limited as mentioned previously. At the same time, the transmitter can generate high voltage across the coil, due to the circuit's ability to switch between a series or parallel connection of the inductor L and capacitor C in the resonant circuit.

Figure 5A:
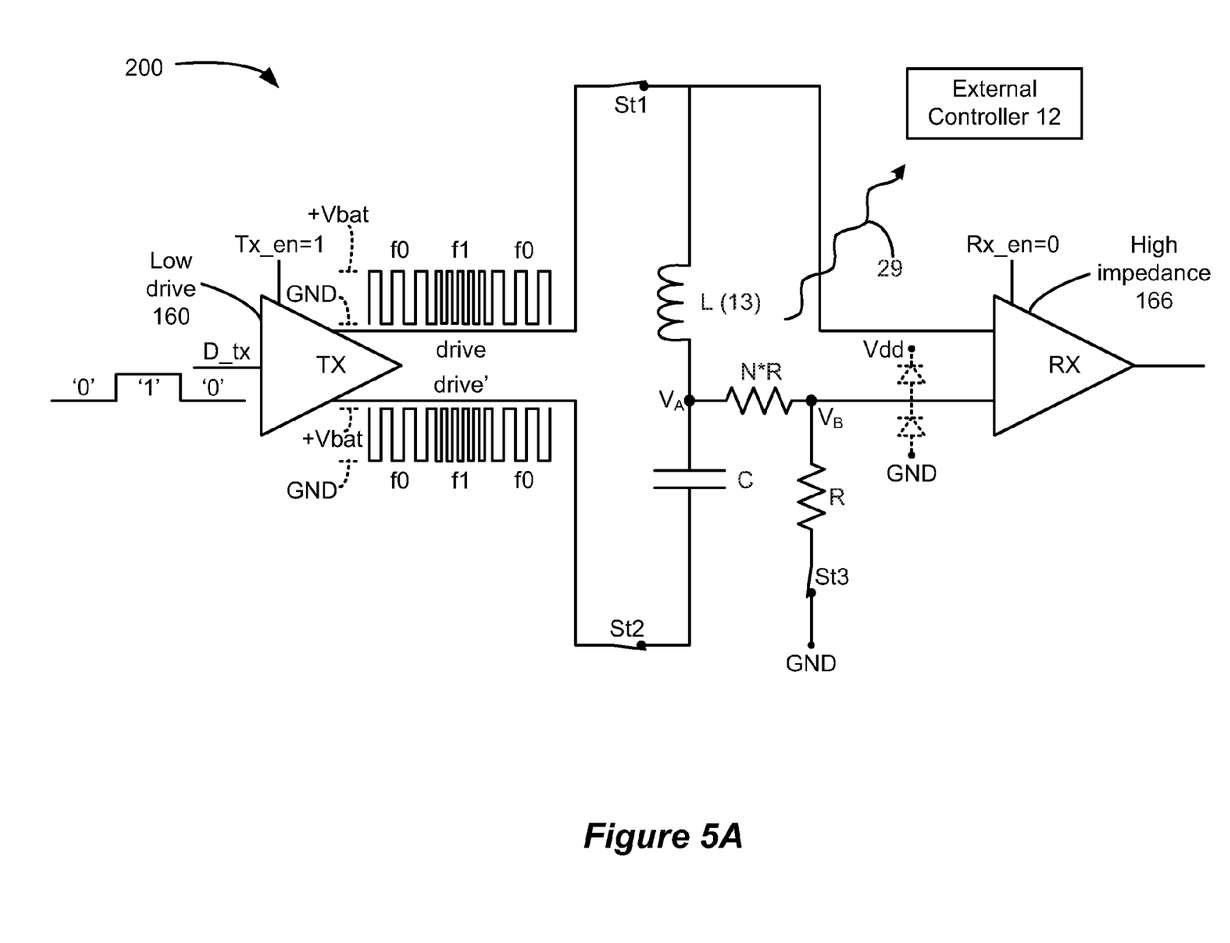
FIGS. 5A and 5B respectively show relevant portions of the improved transceiver circuitry of FIG. 4 in transmit mode and in receive mode.
Figure 5B:
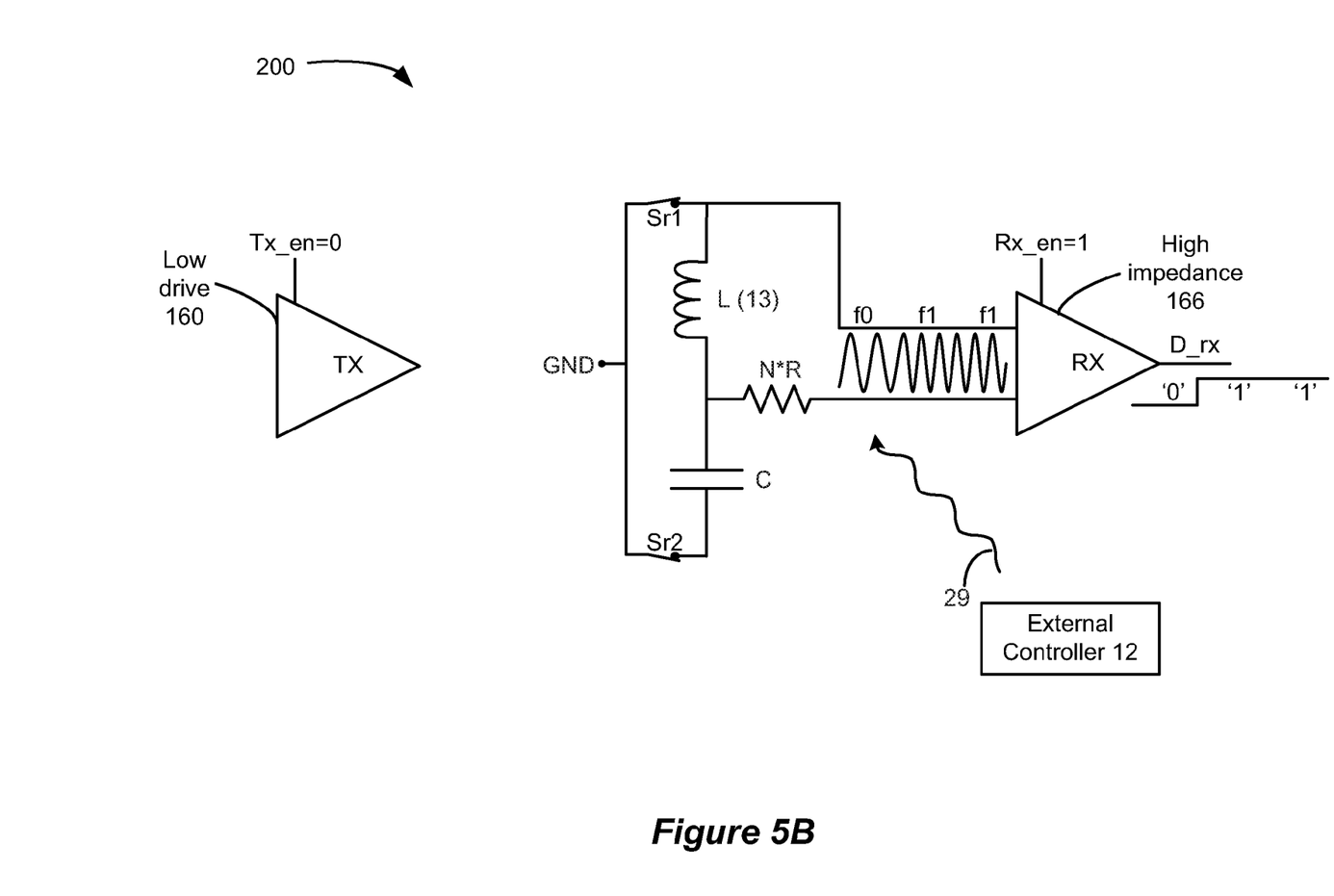

Configuration of the improved transceiver circuit 200 while acting as a transmitter or receiver is respectively illustrated in FIGS. 5A and 5B. Thus, in FIG. 5A, in which the transceiver 200 is acting as a transmitter, the transmitter enable signal (Tx_en) is asserted by the microcontroller 210 along with the control signals necessary to close switches St1, St2 and St3. In FIG. 5B, in which the transceiver is acting as a receiver, the receiver enable signal (Rx_en) is asserted by the microcontroller 210 along with the control signals necessary to close switches Sr1 and Sr2. In both cases, aspects of the circuit 200 that would not be implicated in either of these modes as a result of opened switches are not shown for clarity of illustration.

Referring to FIG. 5A, while transmitting, the closure of switches St2 and St1 connect the inductor L (i.e., the communication coil 13 in the IPG 100) and the capacitor C in series. This allows a low drive transmitter 160 to be used, which as mentioned earlier allows the resonant circuit to be driven by relatively low-level signals, and which minimizes power consumption. However, a relatively large voltage (on the order of +/−50 V) builds up at $V_A$ as explained earlier. Because such a large voltage could damage the receiver 166 at its bottom input, a resistor-based voltage divider is used to trim the voltage $V_A$ to a level $V_B$ at that receiver input. (By contrast, the input at the top input to the receiver is directly connected to the drive signal, which does not exceed Vbat, which is not excessive for the receiver). Specifically, two resistors R and N*R are used. In an exemplary embodiment, R may equal approximately 1 k-ohm and N may equal approximately 100, such that $V_B=V_A/101$, i.e., no more than approximately +/−1 V. Such a voltage range of +/−1 V is well within the operating limits of the high impedance receiver 166, which generally operates at the digital power supply voltage of Vdd (e.g., 2.8V). If necessary to protect the receiver, optional diodes (shown in dotted lines) with thresholds of Vt may be used to ensure that the bottom input to the receiver does not exceed Vdd+Vt and does not fall below −Vt.

Although the series connection of the inductor L and the capacitor C permit high voltages to form at $V_A$, note that none of the switches are exposed to high voltages. For example, opened switches Sr1 and Sr2 (see FIG. 4) must only isolate Vbat from ground. As a result, such switches need not isolate a voltage greater than the power supply voltage and can comprise standard low-voltage switches implementable in the same standard integrated circuitry used to form other logic in the IPG 100. For example, the switches can be implemented on the same integrated circuitry used to form the transmitter 160 and receiver 166. Even though resistors R and N*R will draw some amount of power, choosing their values of suitably high resistance (e.g., in the 100 k-ohm range as discussed) makes current draw through the transistors negligible during periods of transmission. Likewise, when a high input-impedance receiver 166 is used, the receiver 166 does not drain substantial power during periods of transmission.

FIG. 5B illustrates the improved transceiver circuitry 200 when configured in a reception mode. In this mode, switches Sr1 and Sr2 are closed, and the receiver 166 is enabled. Closure of switches Sr1 and Sr2 cause the inductor L and the capacitor C to be connected in parallel, which essentially produces the parallel-configured transceiver circuitry 151 of FIG. 3B, expect for the addition of the additional input resistance N*R provided into the lower input of the receiver, RX. (The voltage divider is inoperable during the reception mode by virtue of St3, which is open). However, the input resistance of the receiver (e.g., >1 M-ohm) is significantly higher than the additional resistance N*R (e.g., 100 k-ohms), such that the additional resistance has negligible effect on reception. Thus, the improved transceiver circuit 200 essentially acts in reception mode as does the transceiver circuitry 151 of FIG. 3B, including the benefits mentioned earlier, such as low power draw and increased reception sensitivity.

As was the case in transmission mode, none of the switches in reception mode are subject to high voltages. Given typical values for the different components, none of nodes in the circuit of FIG. 5B will be higher than 1.0 V for example. Hence, none of the opened switches St1, St2, and St3 (see FIG. 4) need to isolate high voltages greater than the power supply voltage, and thus such switches can comprise standard low-voltage switches implementable in the same standard integrated circuitry used to form other logic in the IPG 100 as discussed earlier.

In summary, the disclosed transceiver circuitry has significant advantages: it can transmit a higher magnetic field with a low drive signal and without excessive current draw through the receiver; it can receive with good sensitivity and low power consumption, and it does so without the needs for specialized or discrete high-voltage components.

Figure 6:
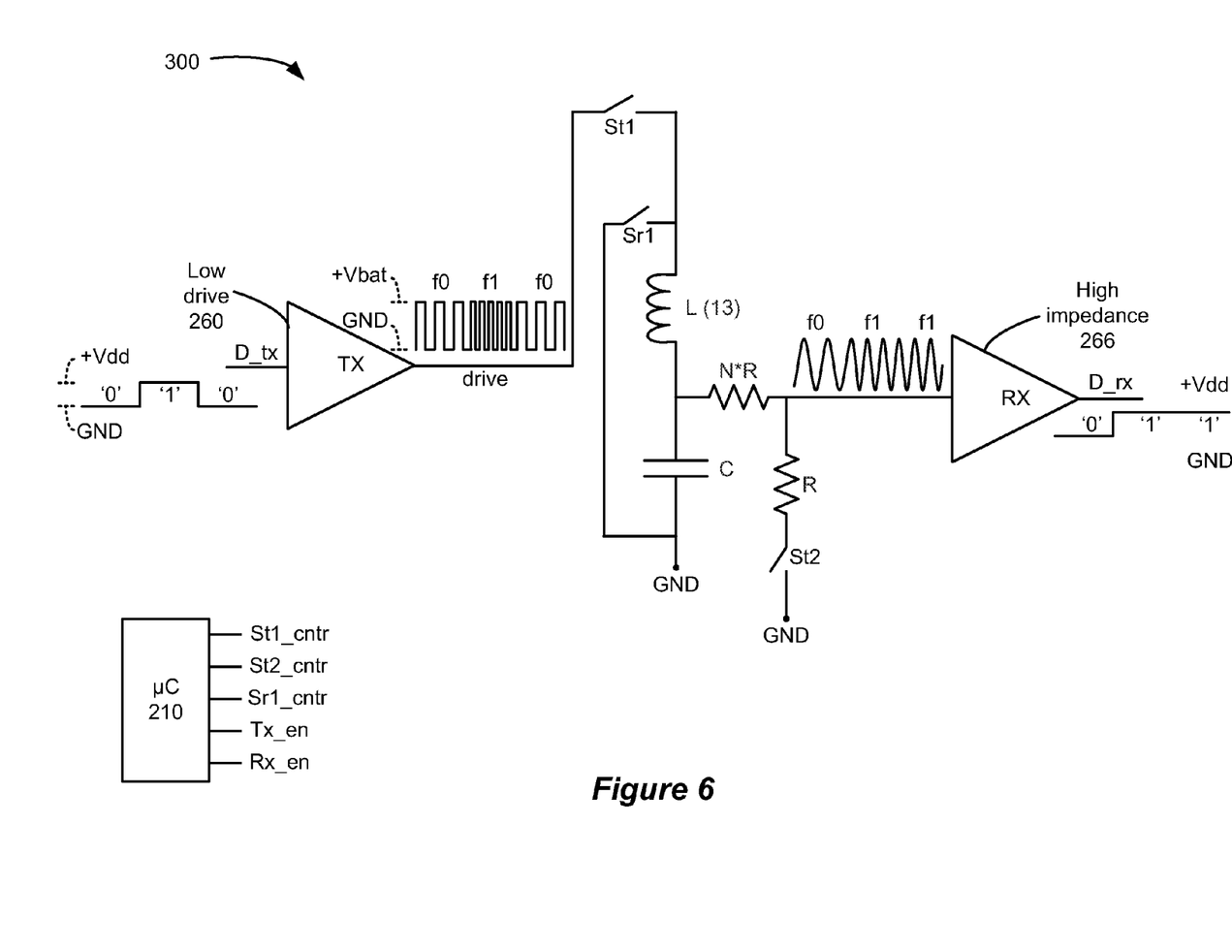
FIG. 6 shows an alternative embodiment of the disclosed improved transceiver circuit having a single output transmitter and a single input receiver.

Although it is preferred to use a transmitter 160 with complementary drive signal outputs, and a receiver 166 with differential inputs, such is not required. Other suitable transmitters 260 useable in the context of the invention can have single drive signal outputs, and other suitable receivers 266 can have single inputs, such as is shown in the alternative embodiment of the improved transceiver circuitry 300 shown in FIG. 6.

Although designed primarily for incorporation into an IPG 100 because of its high efficiency and low power consumption, the improved transceiver circuitry 200 can also be used as the transceiver circuitry in the external controller 12.

While disclosed in the context of a medical implantable device system, it should be recognized that the improved transceiver circuitry disclosed herein is not so limited, and can be used in other contexts employing communications via electromagnetic inductive coupling, such as in Radio-Frequency Identification (RFID) systems, etc. The disclosed circuitry can further be used in any context in which electromagnetic inductive coupling could be used as a means of communication, even if not so used before.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A transceiver circuit useful in an inductive coupling wireless communication system device, comprising:
    a resonant circuit comprising an inductor and a capacitor;
    a transmitter for driving the resonant circuit to produce a transmitted field during a transmit mode;
    a receiver for detecting a received field using the resonant circuit during a receive mode; and
    a voltage divider connected to the resonant circuit for providing a divided voltage from the resonant circuit to an input of the receiver during the transmit mode,
    wherein the inductor and capacitor are coupled in series during the transmit mode,
    wherein the inductor and capacitor are coupled in parallel during the receive mode, and
    wherein the voltage divider is inoperable during the receive mode.

2. The circuit of claim 1, wherein the transmitted and received fields are modulated in accordance with a data protocol.

3. The circuit of claim 2, wherein the data protocol comprises Frequency Shift Keying.

4. The circuit of claim 1, wherein the inductor comprises a communication coil.

5. The circuit of claim 1, wherein the transmitter drives the resonant circuit via complementary drive signals.

6. The circuit of claim 1, wherein the receiver detects the received field via differential inputs provided by the resonant circuit.

7. The circuit of claim 1, wherein the transmitter drives the resonant circuit via a single drive signal.

8. The circuit of claim 1, wherein the receiver detects the received field via a single input provided by the resonant circuit.

9. The circuit of claim 1, wherein the voltage divider divides a voltage at a connecting point between the inductor and the capacitor when in series during the transmit mode to produce the divided voltage.

10. The circuit of claim 1, further comprising at least one switch for coupling the inductor and capacitor in series during the transmit mode and for coupling the inductor and capacitor in parallel during the receive mode.

11. The circuit of claim 10, wherein the transmitter and the receiver are powered by a power supply voltage, and wherein none of the at least one switches isolates a voltage greater than the power supply voltage.

12. A transceiver circuit useful in an inductive coupling wireless communication system device, comprising:
    a resonant circuit comprising an inductor and a capacitor;
    a transmitter for driving the resonant circuit to produce a transmitted field during a transmit mode;
    a receiver for detecting a received field using the resonant circuit during a receive mode;
    at least one switch for connecting the inductor and capacitor in series during the transmit mode and for connecting the inductor and capacitor in parallel during the receive mode; and
    a voltage divider connected to the resonant circuit for providing a divided voltage from the resonant circuit to an input of the receiver during the transmit mode,
    wherein the voltage divider is inoperable during the receive mode.

13. The circuit of claim 12, wherein the voltage divider divides a voltage at a connecting point between the inductor and the capacitor when in series during the transmit mode to produce the divided voltage.

14. The circuit of claim 12, wherein the transmitted and received fields are modulated in accordance with a data protocol.

15. The circuit of claim 12, wherein the transmitter drives the resonant circuit via complementary drive signals, and wherein the receiver detects the received field via differential inputs provided by the resonant circuit.

16. The circuit of claim 12, wherein the transmitter drives the resonant circuit via a single drive signal, and wherein the receiver detects the received field via a single input provided by the resonant circuit.

17. A transceiver circuit useful in an inductive coupling wireless communication system, comprising:
    a resonant circuit comprising an inductor and a capacitor;
    a transmitter powered by a power supply voltage for driving the resonant circuit to produce a transmitted field during a transmit mode;
    a receiver powered by the power supply voltage for detecting a received field using the resonant circuit during a receive mode;
    at least one switch for connecting the inductor and capacitor in series during the transmit mode;
    at least one switch for providing a divided voltage from the resonant circuit to an input of the receiver during the transmit mode; and
    at least one switch for connecting the inductor and capacitor in parallel during the receive mode,
    wherein the divided voltage provided from the resonant circuit to an input of the receiver during the transmit mode is not provided during the receive mode.

18. The circuit of claim 17, wherein none of the switches isolate a voltage greater than the power supply voltage.

19. An implantable medical device, comprising:
    a battery;
    a resonant circuit comprising an inductor and a capacitor;
    a transmitter powered by the battery for driving the resonant circuit to produce a transmitted field during a transmit mode;
    a receiver powered by the battery for detecting a received field using the resonant circuit during a receive mode; and
    a voltage divider connected to the resonant circuit for providing a divided voltage from the resonant circuit to an input of the receiver during the transmit mode,
    wherein the inductor and capacitor are coupled in series during the transmit mode, and
    wherein the inductor and capacitor are coupled in parallel during the receive mode, and
    wherein the voltage divider is inoperable during the receive mode.

20. The device of claim 19, wherein the data protocol comprises Frequency Shift Keying.

21. The device of claim 19, wherein the inductor comprises a communication coil.

22. The device of claim 19, further comprising at least one switch for coupling the inductor and capacitor in series during the transmit mode and for coupling the inductor and capacitor in parallel during the receive mode.

23. The device of claim 22, wherein none of the at least one switches isolate a voltage greater than a voltage of the battery.

24. The device of claim 19, further comprising at least one electrode for stimulating a patient's tissue.

25. An implantable medical device, comprising:
a battery;
a resonant circuit comprising an inductor and a capacitor;
a transmitter powered by the battery for driving the resonant circuit to produce a transmitted field during a transmit mode;
a receiver powered by the battery for detecting a received field using the resonant circuit during a receive mode;
at least one switch for connecting the inductor and capacitor in series during the transmit mode and for connecting the inductor and capacitor in parallel during the receive mode; and
a voltage divider connected to the resonant circuit for providing a divided voltage from the resonant circuit to an input of the receiver during the transmit mode,
wherein the voltage divider is inoperable during the receive mode.

26. The device of claim 25, wherein the voltage divider divides a voltage at a connecting point between the inductor and the capacitor when in series during the transmit mode to produce the divided voltage.

27. The device of claim 25, further comprising at least one electrode for stimulating a patient's tissue.

* * * * *